(12) United States Patent
Njemanze (10) Patent No.: US 6,390,979 B1
(45) Date of Patent: May 21, 2002

(54) NONINVASIVE TRANSCRANIAL DOPPLER ULTRASOUND COMPUTERIZED MENTAL PERFORMANCE TESTING SYSTEM

(76) Inventor: Philip Chidi Njemanze, No. 1 Uratta Road P.O. Box 302, Owerri IMO (NG)

( * ) Notice: Subject to any disclaimer, the term of this patent is extended or adjusted under 35 U.S.C. 154(b) by 0 days.

(21) Appl. No.: 09/935,601

(22) Filed: Aug. 24, 2001

(51) Int. Cl.[7] .................................................. A61B 8/00
(52) U.S. Cl. ...................................................... 600/438
(58) Field of Search ................................. 600/437, 438, 600/453–456, 300, 544, 474

(56) References Cited

U.S. PATENT DOCUMENTS

| | | | |
|---|---|---|---|
| 5,295,491 A | * 3/1994 | Gevins | 128/731 |
| 5,601,829 A | * 2/1997 | Quintana-Almagro et al. | 424/195.1 |
| 5,724,987 A | * 3/1998 | Gevins et al. | 434/258 |
| 5,771,261 A | * 6/1998 | Anbar | 374/45 |
| 6,126,595 A | * 10/2000 | Amano et al. | 600/300 |
| 6,258,032 B1 | * 7/2001 | Hammesfahr | 600/454 |

* cited by examiner

Primary Examiner—Francis J. Jaworski (57) ABSTRACT

A non-invasive method and system to determine the mental performance capacity of a human subject to perform a given task, said method with high temporal resolution, user-friendly and portable, including steps of obtaining a subject's baseline cerebral blood flow velocity in cerebral arteries using a transcranial Doppler ultrasound instrument with sample volumes focused on cerebral vessels on both sides using two probes placed on the temples and calculating laterality index for both arteries. Simultaneously, testing the subject with tasks of mental performance presented on the screen of a digital computer and using a computer input peripheral device while simultaneously monitoring the mean blood flow velocity during each stage of the task in real-time. Processing the acquired data using a microprocessor and communicating the determined mental performance indices via a cellular telephone circuit to a remote computer or mission control.

20 Claims, 8 Drawing Sheets

NONINVASIVE TRANSCRANIAL DOPPLER ULTRASOUND COMPUTERIZED MENTAL PERFORMANCE TESTING SYSTEM

BACKGROUND OF THE INVENTION

This invention is related to computerized systems and methods for determining general intelligence, working memory and psychomotor functions using a portable noninvasive transcranial Doppler ultrasound, microcomputer, an operatively connected cellular telephone, and a computer-aided display. In recent years development of cognitive neuroscience has sort ways to monitor mental performance beyond the conventional neuropsychological approaches. However, monitoring mental performance has not been an easy task. Currently, there is no comprehensive and universal approach for mental performance monitoring. To address this problem more effectively, it is important to understand the basic mechanisms that underlie mental performance. The determinants of human mental performance have been the subject of intense debate for over a century. Spearman (1904, 1923, 1927) suggested that measures of performance or success in diverse cognitive tests show a pattern of almost universal positive correlation. He postulated the hypothesis of a general or g factor making some contribution to success in diverse forms of cognitive activity. This means that people with high g scores will be those usually performing well, although Spearman himself avoided the term intelligence and instead used the term g to refer to the determinants of shared variance among tests of intellectual ability (Jensen, 1987).

Snow et al (1984) constructed an idealized space in which task complexity is maximal near the center and decreases toward the periphery. Psychometric tests including Raven's test and other complex reasoning tests were placed at the center, while simpler tests were placed toward the periphery. Applying this construct, irrespective of the views held by both hypotheses, the centrality of the Raven's test (Raven, 1938) emerges in either case. Furthermore, it suggests that Raven's test is a good measure of intelligence and should account for a good deal of the reasoning in other tests in the center of space (Carpenter et al., 1990). The g factor has since been interpreted as "general intelligence" and refers to a construct underlying a small range of tests, namely those at the center of space.

The concept of general intelligence must have neural anatomic structures for processing of the information. It has been argued that the necessity of keeping several conceptual formulations in mind during Raven's Progressive Matrices (RPM) is itself a working memory function (Carpenter et al., 1990) involving prefrontal cortex (Prabhakaran et al., 1997). Post-rolandic structures may be more critical for this task as shown in patients with brain lesions (Basso et al., 1973). Supportive evidence in normals using positron emission tomography studies have shown that high g tasks do not show diffuse recruitment of multiple brain regions, instead they are associated with selective recruitment of lateral prefrontal cortex in one or both hemispheres (Duncan et al., 2000).

Several recent studies have demonstrated that working memory is typically associated with activations in the prefrontal cortex (PFC), anterior cingulate, parietal and occipital regions (see review by D'Esposito, 2000). These brain areas received blood supply from the middle cerebral arteries. Two fundamental working-memory processes have been identified: the passive maintenance of information in short-term memory and the active manipulation of this information (D'Esposito, 2000).

Motor skill learning is associated with the activation of motor areas of the frontal lobes (Cabeza & Nyberg, 2000), notably the premotor and supplementary motor cortex (lateral and medial Broadman Area 6), and also parietal areas. All these brain areas receive blood supply predominantly from the middle cerebral arteries. Recently, studies using functional magnetic resonance imaging (fMRI) have examined motor skill learning of complex finger movements in piano players and non-musicians (Hund-Gerogiadis & von Cramon, 1999). As learning progressed, piano players showed increased activity in the contra-lateral hand area, whereas non-musicians showed decline in primary motor cortex activation. This may mean that practice-related changes in activity are influenced by pre-practice experience of the subjects.

A study on non-motor skill learning (Fletcher, Buchel, Josephs et al, 1999) investigated changes in brain activity during artificial grammar learning. As subjects learned grammar rules they relied less on memory for specific instances. Learning grammar activated left PFC, whereas reduced instance memory attenuated right PFC (Poldrack, Prabakharan, Seger, Gabrieli, 1999). The visual processing of letters by both hemispheres has been documented using the transcranial Doppler technique (Njemanze, 1996).

Currently, the use of imaging techniques such as positron emission tomography (PET) and fMRI cannot be used a single subject real-time mental performance monitoring under normal everyday conditions. Electrophysiological devices particularly the electroencephalography (EEG) has been used along with other physiological variables such as eye movement, scalp and facial muscle activity, heart activity, respiration and skin conductance to determine the state of mental performance. EEG by itself presents a complexity of parameters and along with other physiological variables have been applied to compare test standards to pretest values. The patent U.S. Pat. No. 5,295,491 to Gevins described a testing method and system for testing the mental performance capability of a human subject, which includes a digital computer workstation for presenting a test to the subject, such as visuomotor memory task. Simultaneously, the subject's physiological variables including brain waves, eye activity, scalp and facial muscle activity, heart activity, respiration and/or skin conductance are analyzed. Test to baseline comparison of the physiological activity and scores are made to determine if the test was passed with a passing score and, if so, whether the subject, in order to pass the test, exceeded a standard based upon the subject's normal mental effort in taking the same or similar test. Similarly, a patent U.S. Pat. No. 5,724,987 to Givens et al. described a computer-aided training system that uses electroencephalograms (EEGs) recorded from the trainee's scalp to alter the training protocol being presented by the computer, for example to present a new task to the trainee when he or she has mastered and automatized the current task. The index of the trainee's skill mastery and automatization is determined by analysis of the EEG using mathematical classification functions, which distinguish different levels of skill acquisition. The functions are computed by computer neural networks and consist of a combination of EEG and other physiological variables, which specifically characterize a trainee's level of focused attention and neurocognitive workload and his "neurocognitive strategy". The functions are derived either for a group of trainees, or each trainee individually, performing a battery of one or more standard training tasks while wearing an EEG hat.

The term "neurocognitive" has been defined as those mental functions for which physiological indices can be measured and "neurocognitive workload" as the level of neural activation associated with mental effort as described in U.S. Pat. No. 5,724,987 to Givens et al. The "critical limit of neurocognitive workload" refers to a measurable cutoff point after which error rates on the task appear to rise dramatically in combination with change in neurocognitive strategy. The term "neurocognitive strategy" refers to the hemispheric strategy (hemisphere advantage) a subject uses to perform a task. Neurocognitive strategy is characterized by a cerebral blood flow increase in a given hemispheric region relative to the other hemisphere; it might be either in the left or right brain or bilaterally. Givens et al in U.S. Pat. No. 5,724,987 used the phrase "skill acquisition and automation" to denote a high degree of skill mastery in which a high level of performance and focused attention can be maintained with a relatively low level of task-specific neurocognitive workload.

'Mental performance' refers to a cumulative physiologic brain response in a subject performing tasks of cognitive functions including linguistic, non-linguistic, visual, auditory or psychomotor stimuli. The term natural intelligence refers to mental performance in a human subject accompanied with detectable lateralization changes in cerebral blood flow velocity. The term enhanced natural intelligence systems (eNI) refers to computer programs and operating systems that are interfaced with natural intelligence in a manner that will enhance overall performance of the subject and efficiency of the programs. The term artificial intelligence refers to computer models of brain function that uses adjustable weighted connections to learn and remember. The model when organized in 'neuronal circuits' comprising one or several neurons in a network is referred to as neural networks. A 'hybrid neural network' is a neural set with crisp signals and weights and crisp transfer function. A 'hybrid fuzzy neural network' is a neural network with fuzzy signals and/or fuzzy weights. A processing element of a hybrid neural net is called 'fuzzy neuron'. The hybrid neural nets can be used to implement fuzzy IF-THEN rules in a constructive way. The hybrid neural nets can be trained by steepest descent methods to learn the parameters of the membership function representing the linguistic terms of the rules. The term 'hybrid natural and artificial intelligence systems (hNI)' refers to computer programs and operating systems that use fuzzy and neural network systems to process inputs of perceptual and natural intelligence to realize output of performance indices. The term 'mental signature' refers to the highly sensitive and specific characteristics of the mean cerebral blood flow velocity changes and derived laterality indices in response to a particular task presented to a given individual and providing high reproducibility on repeated testing in the same subject. In other words, the term 'mental signature' refers to the pattern of changes of neurocognitive strategy in response to tasks in a given subject with high sensitivity, specificity and reproducibility. The neurocognitive strategy used by a subject could describe the subject's 'state of being' at any given time. The neurocognitive strategy used for processing a task with the resultant best performance indices is described as the 'best state of being'. Having determined the neurocognitive strategy and workload, the proximity to the critical limit will determine the necessity to change "autonomy decision-making level" from an operator to an automated system. The term "autonomy decision-making level" refers to the level of independence a subject/operator has to take decisions without intervention of a "command-and-control unit" or his ability to override automated tasks on a host computer. The term "command-and-control unit" refers to a group of human operators who are involved in definition of mission strategic and tactical objectives, the term is used interchangeable with "mission control".

Prior art does not monitor in real-time general intelligence, working memory or psychomotor functions under usual conditions. The prior art electrophysiologic monitoring methods are based on multiple physiologic variables and hence increasing the potential sources of technical artifacts. The prior art based on EEG and other physiologic variables are somewhat technically impractical since the multiplicity of electrodes restricts movement and normal behavioral activity. The applicability of prior art is based on detection of change from a normative baseline that could be conditioned by a number of factors including such poorly understood areas of cognitive neurosciences such as emotion and overall consciousness. Thus, another difficulty not resolved by presently available techniques is the determination of overall rules governing neurocognitive strategy in mental performance tasks. Without such a determination of the governing rules multiplicity of factors make it difficult of make a reliable prediction based on observed physiologic change. It must also be noted that EEG based approaches are rather technically and physiologically complex and difficult to interpret for everyday applications.

There is presently no means for real-time monitoring of motor skill learning that could be easily implemented in a normal condition for example in a classroom training session. Both fMRI and PET can only be implemented for this purpose in a special circumstance and extensive preparation is required for EEG based systems. The portability of even the smallest versions of EEG remains a major obstacle to its use for monitoring under usual circumstances.

Assessment of complex perceptual learning tasks such as that during a video game in real-time under home conditions cannot be implemented with prior art. Similarly, real-time monitoring of linguistic processing during a classroom learning session could not be practically implemented with fMRI, PET or EEG. The latter instrumentations are for hospital-based conditions or specially arranged circumstances.

The issue of cost-effectiveness is a considerable and probably even an overriding factor that makes fMRI, PET and EEG-based technologies non-applicable for everyday real-time monitoring.

BRIEF SUMMARY OF THE INVENTION

There is currently no method to determine the governing principles of mental performance and a unified approach to determine compromised performance other than changes to a normative baseline. Electrophysiological techniques in spite of good temporal resolution fail to define a unified set of rules governing good versus bad mental performance. Neuroimaging techniques (PET and fMRI) are cumbersome and have poor temporal resolution so are not applicable for monitoring performance in real-time man-machine interface systems. Indeed, what is required is a non-invasive technique that is easy to use for everyday applications, and would not involve extensive wiring of the subject. Such a technique must allow man-machine interface that will permit easy and fast computation of subject's mental performance and communication to a human observer or a host computer. The said system must have high predictability of imminent compromised mental performance. The use of similar man-machine interface systems for example in modern high performance avionics may well improve overall aircraft performance and more importantly prevent aircraft mishaps due to pilot error. Such as has been described by U.S. Pat. No. 5,121,744 to Njemanze P C. For on-line monitoring in man-machine automated systems, it is essential that complexity of the variables monitored be kept low in order to minimize potential sources of artifacts or to eliminate them all together. Multi-parameter monitoring of different physiologic functions although desirable in some cases are non-specific and probably less useful compared to a pinpoint monitoring of brain blood flow velocity indices of mental performance. It is also vital to have a technique that predicts overall "neurocognitive" strategies allowing pre-test classification of subjects and prediction of expected results with greater specificity and sensitivity. The said neurocognitive strategy at each level of task has some specificity for each individual depending on the approach to problem solving. This can be used as a mental signature. The latter provides a unique physiologic identity of the subject as much as is his/her fingerprint by way of example. This said physiologic identity could be used when logging on a computer network. A network of several individuals making mental inputs into a computer system can then be processed using fuzzy and neural network systems as described in book by Robert Fuller entitled "Advances in Soft Computing—Introduction to Neuro-Fuzzy Systems" and published by Physica-Verlag, of Heidelberg, N.Y., dated 2000.

Transcranial Doppler (TCD) sonography is an ultrasound technique that uses Doppler principles to measure cerebral blood flow velocity in major brain arteries of the circle of Willis. The basic principles and common clinical applications are detailed in a book edited by Aaslid R, entitled "Transcranial Doppler Sonography" and published by Springer, of Wien, N.Y., dated 1989, on pages 39 through 50. There is increasing body of evidence that cerebral lateralization can be studied using transcranial Doppler ultrasound (Njemanze, 1991; Njemanze, Gomez and Horenstein, 1992; Njemanze, 1996; Evers et al., 1999; Vingerhoets and Stroobant, 1999). Studies with TCD have been cross-validated by functional MRI (Schmidt, et al., 1999) and reproducibility assessed (Knecht, et al, 1998).

OBJECTIVES AND FEATURES OF THE INVENTION

It is an objective of the present invention to provide a method and system that uses real-time measurements of cerebral blood flow velocity in major arteries of the brain for example middle cerebral arteries to measure general intelligence.

It is a further objective of the present invention to provide a method and system that uses real-time measurements of cerebral blood flow velocity in major cerebral arteries of the brain (for example the middle cerebral arteries) to make a distinction between true and false answers to a task presented to a subject.

It is a further objective of the present invention to provide a method and system for measuring working memory in order to communicate to a host computer or an interested observer for task proficiency assessment.

It is a feature of the present invention to provide a method and system for measuring working memory in order to communicate to a host computer for change of autonomy decision-making level in an automated system or mission control.

It is feature of the present invention to provide a method and system for measuring impairment of working memory in subjects or patients with memory deficits.

It is a further feature of the present invention to provide a method and system for measuring improvement of working memory due to interventional procedures or use of pharmacological agents.

It is a further feature of the present invention to obtain the physiologic parametric measure of skill acquisition and automation during mental performance of a task.

It is a further feature of the present invention to determine neurocognitive workload of a test subject in order to determine the critical limit of neurocognitive workload.

It is a further feature of the present invention to determine the hemisphere (right or left) used by a subject for processing a specific task and to determine the effectiveness of task performance, and to explain factors contributing to decrements in performance.

It is a further feature of the present invention to determine the effect of perceptual and motor tasks on mental performance for design of perceptual and motor tasks that has mutually synergistic effects on mental performance.

An object of the present invention is to determine the effect of extreme environments on mental performance. Examples of 'extreme environment' include determining the effects of microgravity, high-altitude and deep sea diving on mental performance, and assessment of cognitive, physiologic and pharmacological methods for effective counter measures.

Another object of the present invention is to provide a computer-aided training system for subjects using real-time physiologic blood flow velocity correlate of performance as the criteria for altering the level of task difficulty presented to a subject. That could be implemented for educational, industrial and entertainment purposes.

Another object of the present invention is to provide a real-time cerebral blood flow velocity correlate of mental performance that could be integrated in videogames for upgrading or downgrading the level of task difficulty presented to a 'player' or subject. The latter is essential for individualizing physiologic responses in videogames used on play stations for adults and children.

It is yet another object of the present invention to provide a cerebral blood flow velocity measure of mental performance on a task presented in a virtual environment generator in order to assess the different responses and optimize real-world task conditions used for design of materials including by way of example music, automobile, houses, designer clothes etc.

Yet another feature of the present invention is to provide a cerebral blood flow velocity index of performance on motor skill learning of increasing complexity in normal subjects and patients with motor impairment such as after a stroke brain lesion.

Yet another feature of the present invention is to provide a cerebral blood flow velocity index of mental performance on a visual linguistic task in healthy subjects or aphasic patients such as after a stroke brain lesion.

A further feature of the present invention is to provide a cerebral blood flow velocity index of mental performance of a visual non-linguistic task in health subjects or patients such as after a stroke brain lesion.

It is a further feature of the present invention to provide a portable instrument for monitoring mental performance that could be a personalized carry-on device for monitoring individual mental performance.

It is yet a further feature of the present invention to provide a cost-effective instrument for monitoring mental performance that could be affordable for home use.

It is yet a further feature of this invention to provide a user-friendly instrument for mental performance monitoring that is easy to operate and interpret without any specialized training.

It is a further feature of the present invention to provide a non-invasive instrument for mental performance monitoring that could be used repeatedly for several hours in a day.

It is a further feature of the present invention to provide a real-time mental performance-monitoring device that has a high temporal resolution.

It is yet another feature of the present invention to provide a mental performance monitoring device that could be connected to a network via the Internet, linking several subjects simultaneously to a host computer or mission control.

It is another feature of the present invention to provide a means to determine mental performance of workers and use the said information to organize a production process in order to improve quality management through determination and efficient use of time of maximal productivity and use of time of low productivity for recreation.

It is another feature of the present invention to determine the mental performance of workers in a production process for motion and time studies to more efficiently organize tasks by matching task difficulty to the state of mental performance.

It is another feature of the present invention to determine mental performance for use in personal organization of schedule and programs, to maximize use of periods of the day with highest mental performance to perform the most mentally demanding tasks.

It is another feature of the present invention to determine the mental performance for understanding of an individual's biorhythm with exact determination of periods of the day with highest efficiency and those with lowest efficiency dependent on the circadian rhythm of the individual.

It is another feature of the present invention to determine the mental performance of subjects on a mission in order to assess the mental health status of the individuals, their exact location and the capacity to accomplish the mission.

It is yet another feature of the present invention to determine mental performance of a subject and communicate it via a cellular phone to a host computer for mission control.

It is another object of the present invention to determine the mental signature of a given subject that could be used as a personal physiologic identity when logging on to a network of restricted access.

It a further object of the present invention to use the mental signature of a subject to provide computer network security including financial, military, top government computer network and major businesses.

It is a further object of the present invention to process mental performance of several subjects making an input in a computer system using fuzzy and neural network systems for optimization of the production processes.

It is a further object of the present invention to process mental performance of a subject making an input in a computer system for mental signature recognition.

It is a further object of the present invention to process mental performance of a subject making an input in a computer system for recognition of best state of being.

DETAILED DESCRIPTION OF THE INVENTION

Figure 1A:
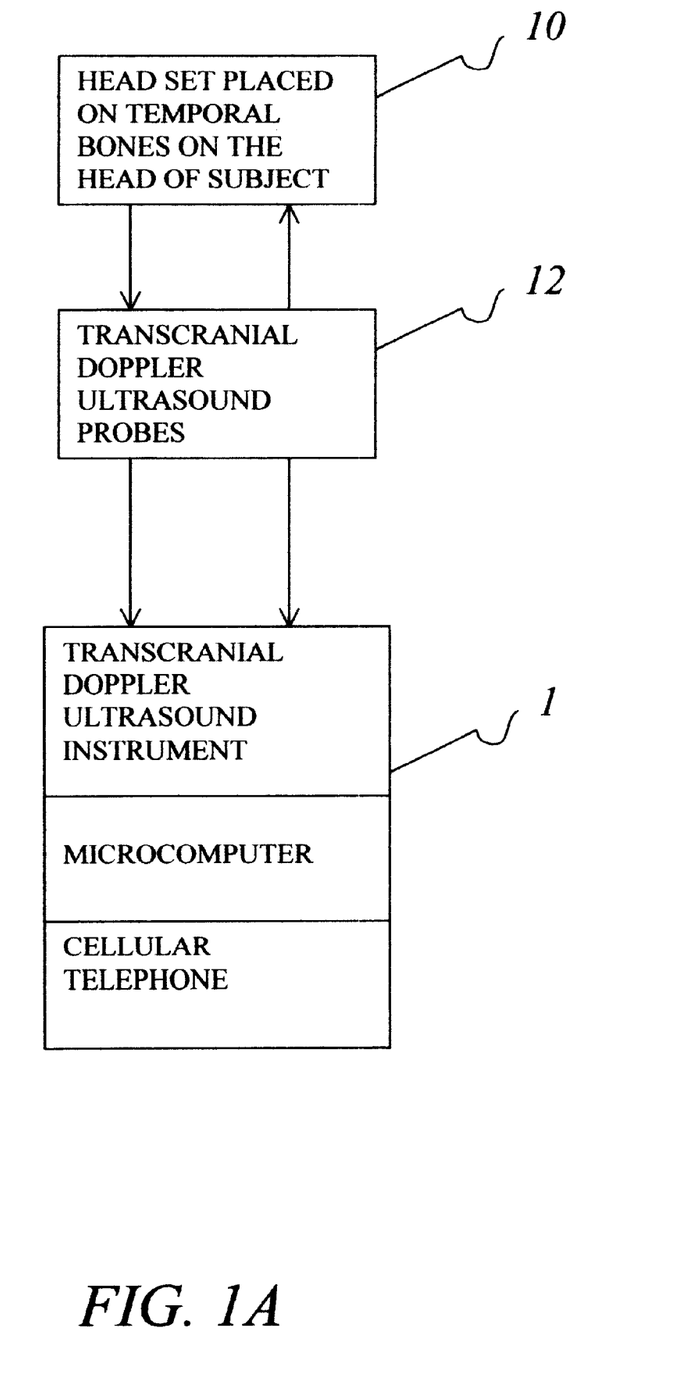
FIG. 1A is a block diagram schematically representing the present invention.
Figure 1B:
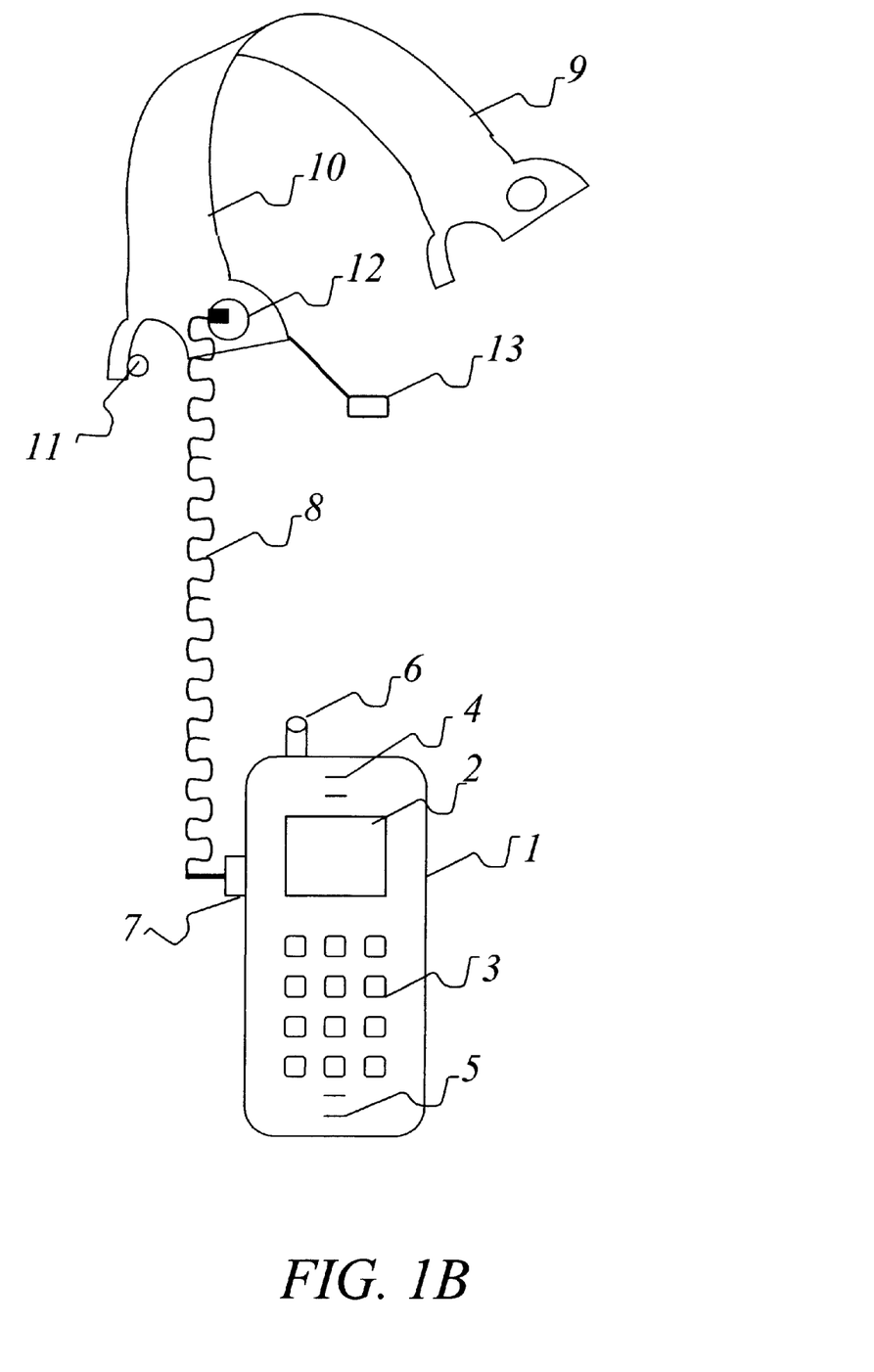
FIG. 1B is a schematic representation of the system according to the present invention.
Figure 2:
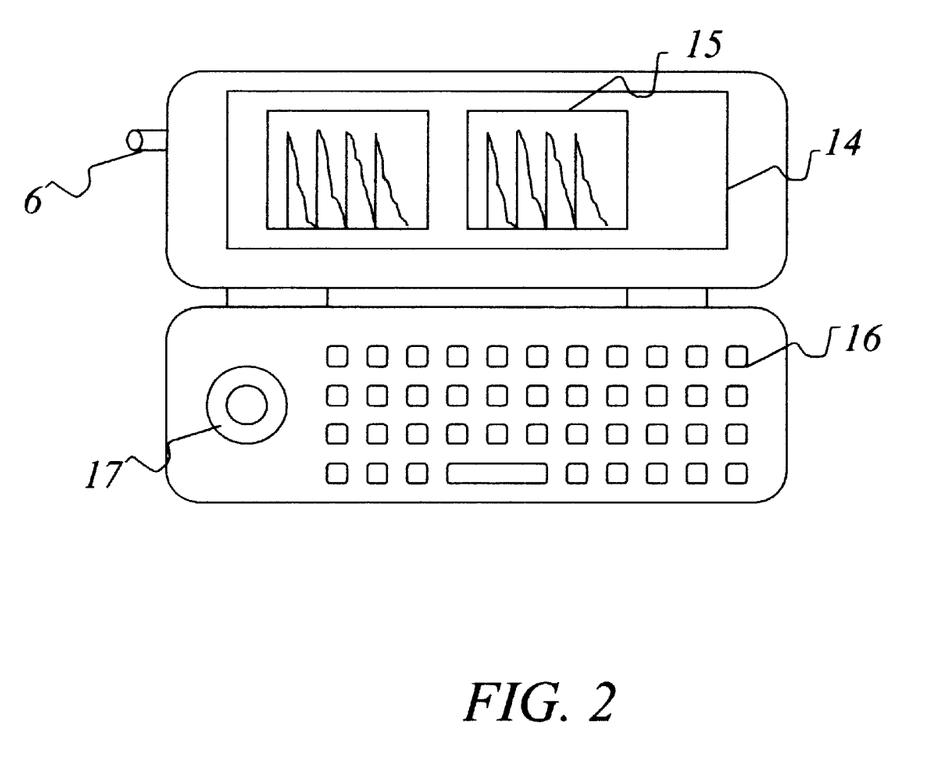
FIG. 2 is a schematic representation of one possible embodiment of the present invention.

The block diagram of the present invention is illustrated in FIG. 1A. As shown therein, a head set 10, is placed on a human subject who wears the head set with two transcranial Doppler probes 12 attached and focused on the cerebral arteries for example the middle arteries (MCAs) from both sides of the head on the temporal bones above the zygomatic arch. The sample volumes of the pulsed Doppler could be placed at a depth of 50 mm from the surface of the probe on both sides. The probes are covered with ultrasonic gel to enhance tissue coupling. A suitable head set has been described in the inventor's U.S. patent application Ser. No. 09/483.764, filing date Jan. 14, 2000, Art Unit No. 3737 and incorporated in the reference herein. The headset steers the probe by automated insonation of the cerebral vessels and is controlled by a microcomputer connected with the transcranial Doppler instrument (TCD) and the cellular telephone circuit as a functional unit 1. The TCD instrument is a miniaturized version of commercially available systems from several manufacturers. A miniaturized TCD with bilateral probe insonation can be obtained from a company called DWL (Sipplingen, Germany) by way of example. The TCD is physically connected to a cellular phone circuit as one unit similar to the cellular phone packaging offered by Nokia (Finland) and both connected devices could be controlled by a common microprocessor such as the Pentium series from Intel Company, of San Jose, Calif. by way of example. This combination creates a new device according to the teachings of the present invention that is a hybrid of microcomputer-transcranial Doppler-cellular phone. As shown in FIG. 1B, the cellular telephone has the normal features of a cellular phone with an LCD display 2, a dial keypad 3, a loudspeaker 4 and a microphone 5. An aerial receiver 6 for microwave reception could also has additional capability such as transmission of the user's position using global positioning system (GPS) as a new feature. The present invention is connected to the head set with left and right arms on the left temporal 9 and right temporal 10 bones via a wire 8 attached to the probe 12 and head set from a detachable site 7 on the device 1. While the device is in use the subject can hear via an earphone 11 and make voice communication via a microphone 13. The invention as seen from the inside in FIG. 2, has two parts when opened, the top front part is the cellular phone device, the top back from inside is an LCD display 14, for showing the flow velocity waveforms from both cerebral arteries 15. The second lower part houses the TCD instrument and the microcomputer with attached alphanumeric keyboard 16 and cursor control 17 provided on the keyboard. The sound of the TCD instrument from the Doppler signals can be heard on the loudspeakers 4 and 11 during setup time. Other features like internet connectivity, personal organizer and communicating with other computers are set by the various programs loaded on the device of the present invention using the keyboard 16 and larger LCD display 14. The invention uses the full advantage of the cellular telephones include internet connectivity, uploading of the Doppler ultrasound images and flow trend analysis and also down-loading of instructions and tasks from a host computer or a website on the internet.

Figure 3:
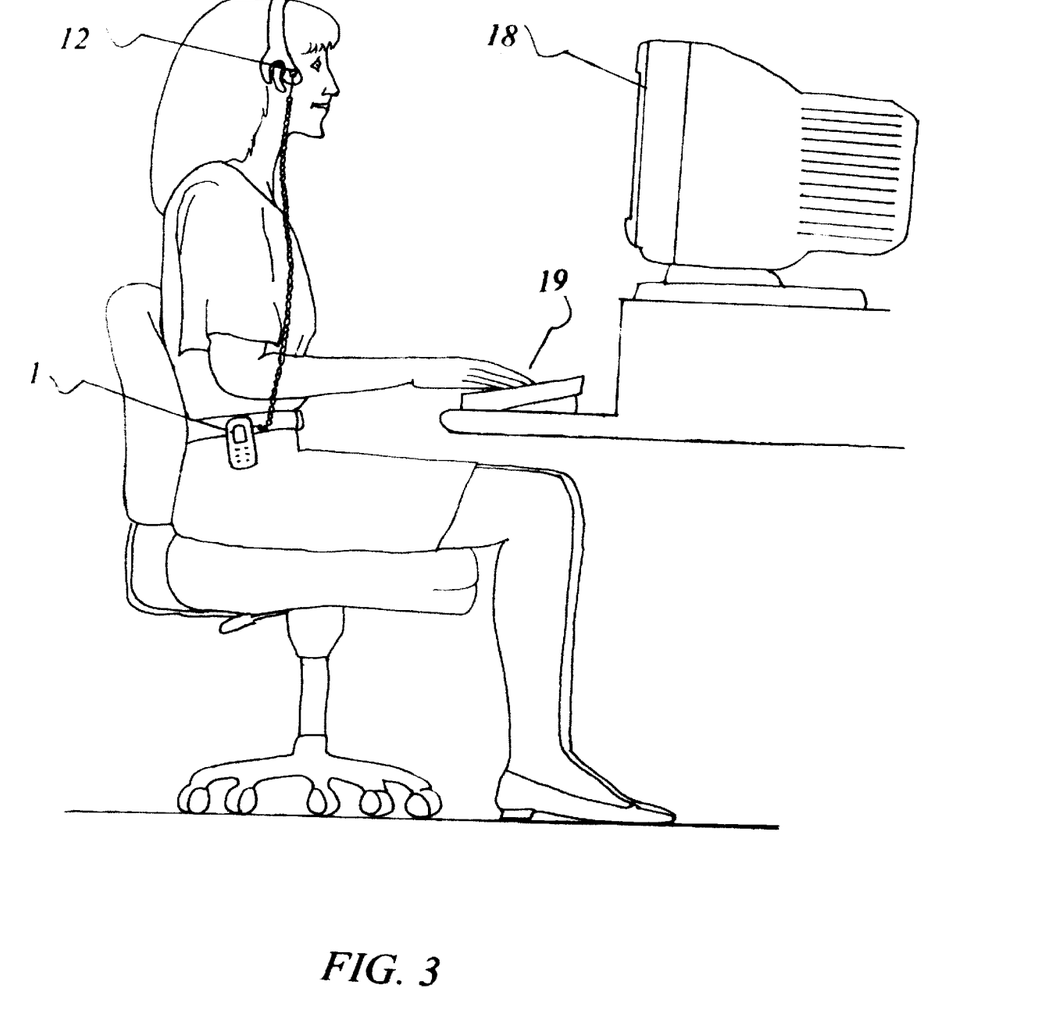
FIG. 3 is a schematic representation of the present invention showing person-to-computer interface.

The use of the device of the present invention by a subject interfaced with a personal computer is illustrated in FIG. 3. The device 1 is worn on the subject's waist belt by way of example with the TCD probes 12 attached to a headset. The subject performs a task by visualizing the task on a computer monitor 18 and entering the required information via a mouse or keyboard 19.

The subject could also be working on a workstation of virtual environment for task and material designs requiring optimal mental performance. The virtual environment could be provided by a high-performance 3-D graphic workstation such as Indigo Extreme$^2$ Graphics Workstation, Model R4400, and Performer Software, Silicon Graphics, Inc., Mountain View, Calif., by way of example. Other possibilities of virtual environment generators include: head mounted visual display such as Model 100pv VIM Personal Viewer, Kaiser Electro-Optics, Carlsbad, Calif.; head-mounted acoustic display which provides spatial display of sound sources in 3-D such as Convolvotron, Crystal River Engineering, Groveland Calif., and can be used with other elements of a virtual environment generated graphic workstation. Psychomotor functions could be tested in conjunction with the present invention using a computer device that recognizes hand shapes and orientation and coverts them to a computer readable form and allows subjects to manipulate and interact with virtual objects called hand shape and orientation transducer (input device) such as that from Cyber Glove, Virtual Technologies (Virtex), Stanford, Calif. Other possible psychomotor performance testing with the present invention include a hand-held human interface used to input 6-degree-of-freedom position and orientation information of users' hand into a virtual environment simulation and to display interactively reactivity computed forces and torques, such as the JPL Model X Force-reflecting hand controller, Teletechnologies, San Pedro, Calif.

Figure 4:
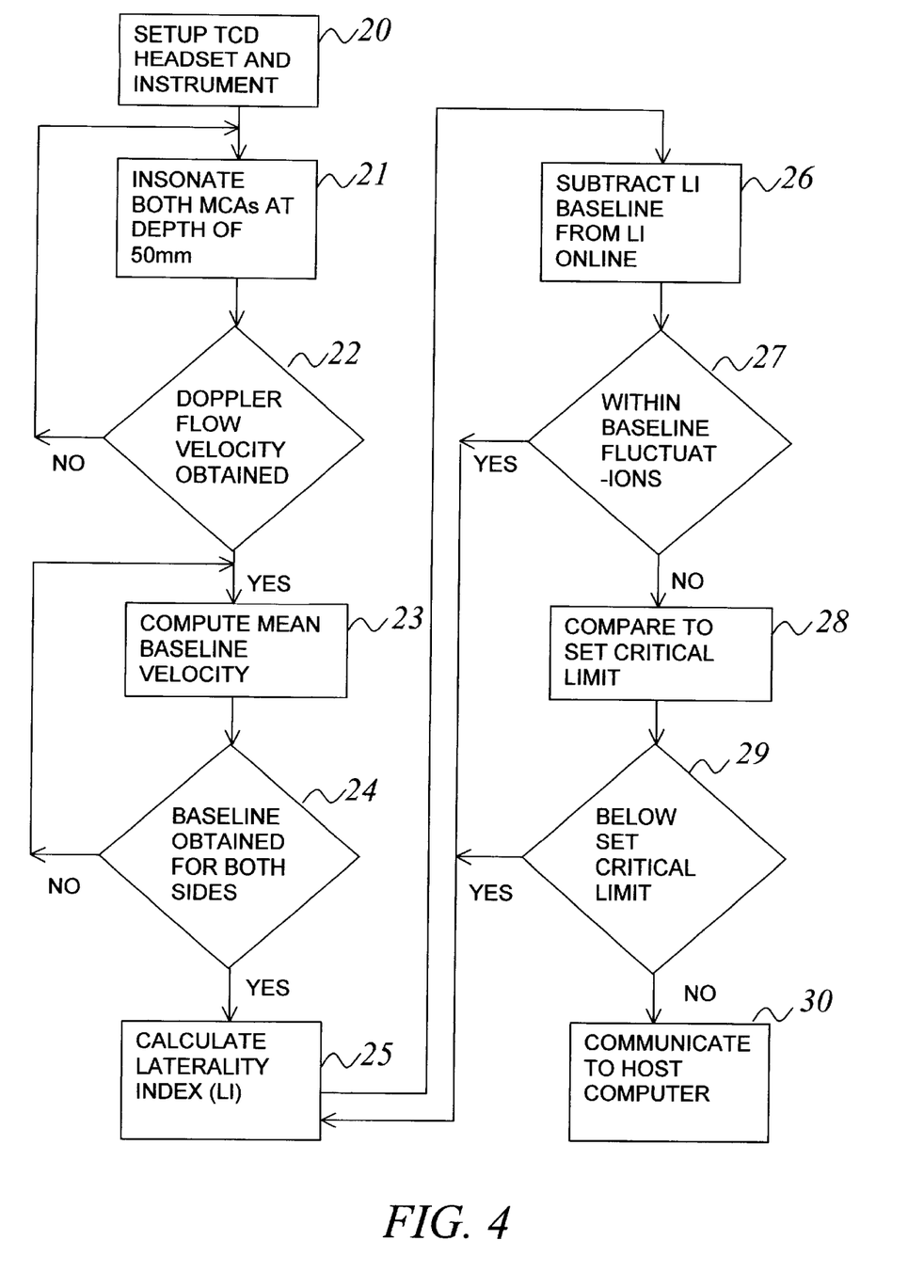
FIG. 4 is an example of a functional flow chart of the present invention.

The functional flow chart of the present invention by way of example is seen in FIG. 4. After the setup of the headset and the device of the present invention as shown 20 both MCAs are monitored and the MBFV determined at a depth of 50 mm 21. If the MBFVs determined are from flow waveforms of good Doppler signal quality 22, then the system proceeds to compute a mean baseline MBFV for the time resolution set, for example every 10 seconds 23. If not, the system prompts for a search for a better signal quality 22 in automated fashion for example as described in the inventor's U.S. patent application Ser. No. 09/483.764, filing date Jan. 14, 2000, Art Unit No. 3737. The device should establish the baseline for both sides 24, and may repeat the steps if required until a satisfactory baseline value is obtained 24 before it proceeds to calculate the LI for baseline and online measured MBFV 25 given by the formula (see also below):

$$LI'=(\text{Right MBFV}_{10sec}-\text{Left MBFV}_{10sec}/(\text{Right MBFV}_{10sec}+\text{Left MBFV}_{10sec}))*100.$$

The system determines the LI' for baseline and online (task) measured MBFV values. And performs a calculation of the relative change in LI 26 related to the task given by:

$$LI=LI'\text{task}_{10sec}-LI'\text{baseline}_{10sec}$$

If the obtained LI is within the limits of baseline fluctuations 27 the system repeats calculation of online LI values 25 and repeats in the same fashion. If the obtained values are above baseline LI limits 27 then the system proceeds to compare the online LI values with set critical limit of LI 28, for example the critical limit of neurocognitive workload. If the online LI value is below 29 the set critical limit the system proceeds to calculate new online LI 25. If the calculated LI is above the set critical limit the system communicates the data to a host computer 30 as ensuing compromise in mental performance status. This information is made use of in a number of ways including to change the autonomy-decision making level between a pilot and an autopilot, or astronaut and mission control, by way of examples. As in the example in FIG. 3 a female subject is most likely to use the left hemisphere to solve the presented tasks. The lateralization of cerebral blood flow is to the left MCA with LI values showing left hemisphere advantage or a left neurocognitive strategy. As task difficulty increases the left hemisphere advantage increases and facilitates correct resolution of the presented tasks. However, if the tasks cannot be resolve there is a bi-hemispheric (left and right MCAs) activation or only a contralateral right MCA activation. This will suggest that the critical limit of neurocognitive workload has been reached and there is a likelihood of increasing error rates. The device of the present invention detects the onset of the bi-hemispheric activation and communicates via the system microprocessor and the cellular phone by wireless transmission to a host computer or a computer interfaced with the subject. The computer is equipped with a wireless transmission so that exchange of data with the cellular telephone is possible. A program in the computer to for example may alter the next level of task to be administered. Other possible options are termination of the task if the critical limit for error tolerance is reached, regulation of autonomy-decision making levels between the subject and mission control or an automated systems such as in computerized avionic systems and in modern aircrafts between autopilot and the human pilot. Simpler uses of the device could be in computer operating systems and word-processors. Whereby increasing error rates in spelling coupled with mental performance decrements could activate Help programs that could use the content of the draft and a few categorical clues to construct a letter or other texts more efficiently and suggest the options to the user. This will create intelligent word processors rather than the conventional ones available now. Similarly, the operating systems could use the said information to communicate to several other programs including spreadsheets and statistical programs, which can suggest solutions to the user in a more efficient manner than that used until now. In other words, new intelligent computer systems and programs could be built with human-computer interface providing hybrid natural and artificial intelligent systems. Similarly, video game play stations such as that from Sony Corporation (Play station II), Microsoft, Nintendo and other manufacturers could use the information from the present invention on the mental status of the subject (game player) to upgrade or downgrade the game level. This will make for healthier entertainment with no detriment to mental processing. Further use of the information can be seen when a number of individuals are linked via an office network to perform complimentary tasks and one or more individuals approach the critical limit of neurocognitive workload as determined by the present device. Others could relieve these individuals and the process continued without interruption and introduction of operator errors. Such a regulation could be very essential in critical situations such as that faced by air-traffic controllers, stock brokers, media correspondents, workers at nuclear plants and medical personnel teams.

Mission control in the military could also benefit from determination of mental performance status as described.

A detailed description of an experiment to determine performance on Raven's Progressive Matrices by way of example of an intelligence and working memory task is set forth below.

Intelligence and Working Memory

Materials and Methods

Study Population

The population consisted of 24 subjects of which 15 were females and 9 were males, their age ranging between 21 and 33 years (mean±SD=25.08±3.16 years); females (25.47±3.5 years) did not differ from males (24.44±2.5 years) by age. Handedness was determined using the Edinburgh handedness inventory (Oldfield, 1971). No subject had any history of neurological or cardiovascular or respiratory diseases. The medical history revealed no long-term use of any medication, including contraceptive pills for females. All were instructed to abstain from ingesting caffeine at least 24 hrs prior to the study. All were non-smokers and did not abuse alcohol. All have had at between 16–18 years of schooling. All signed informed consent according to Declaration of Helsinki. Institutional Ethical Committee approved the study.

Recording

In a briefing held before the start of the study all subjects were informed on the protocol for the entire experiment and all detail explained on the requirements questions for the RPM paradigm. All TCD studies were performed using examination techniques similar to those previously published (Njemanze, 1991) and using a new bilateral simultaneous TCD instrument similar to the present invention described above. First, the subject was placed in supine posture on bed with head up at 30 degrees. The probe holder headgear was placed on the temples on both sides, two 2 MHz probes were affixed in the probe holder and insonation performed to determine the optimal position for continuous insonation of both MCA main stem at 50 mm depth from the surface of the probe. All gain and power settings were kept constant for both MCAs in all subjects. The probes were locked in position after adjusting the lever and tightening the knurled screw from both sides. Comfort of the subject within the headgear was assured prior to start of recording. Subjects were instructed not to move or talk throughout the data acquisition time duration. All recordings were carried out with exclusion of all environmental noise including sound from the TCD instrument, and environmental luminance was kept constant for all participants. Electrocardiographic recordings of heart rate and respiratory rate were monitored along with self-perceived anxiety levels during the study to control for effects on results. Measurements comprising a continuous train of velocity waveform envelopes were recorded at resting baseline with the subject mute, still and attention focused on a cube target projected on a screen with no mental or manual tasks to perform.

Task Paradigms

During the RPM paradigm, subjects were shown patterns in a 3×3 cell matrix with a missing piece [see, for example Raven (1938); Carpenter et al (1990) for sample stimuli]. Only eight black and white tasks (Numbers: A5, A9, B4, B7, C8, D8, E9, E11) were administered by projecting on a screen. The stimulus duration time per RPM task was 60 seconds. None of the subjects has ever solved RPM or similar intelligence tests prior to this study. Success during RPM paradigm required the subject to perceive the relationships between cells in the matrix, determine the relationships between the columns and rows of the matrix and then integrate this information. They were required to determine which of the six to eight possible alternatives best completes the matrix so that the inter-relational rules among the elements between the row and columns were meet. No verbal answers were required, instead subjects were asked to indicate their choice of option by finger tapping the option chosen.

Statistics

Results were given as mean±SD where applicable. The LI scores were analyzed using multivariate analysis of variance (MANOVA). When applicable group means were compared using t Test. All statistical calculations were done using a statistical software package (Statistica, StatSoft, OK, USA).

Results

Figure 5A:
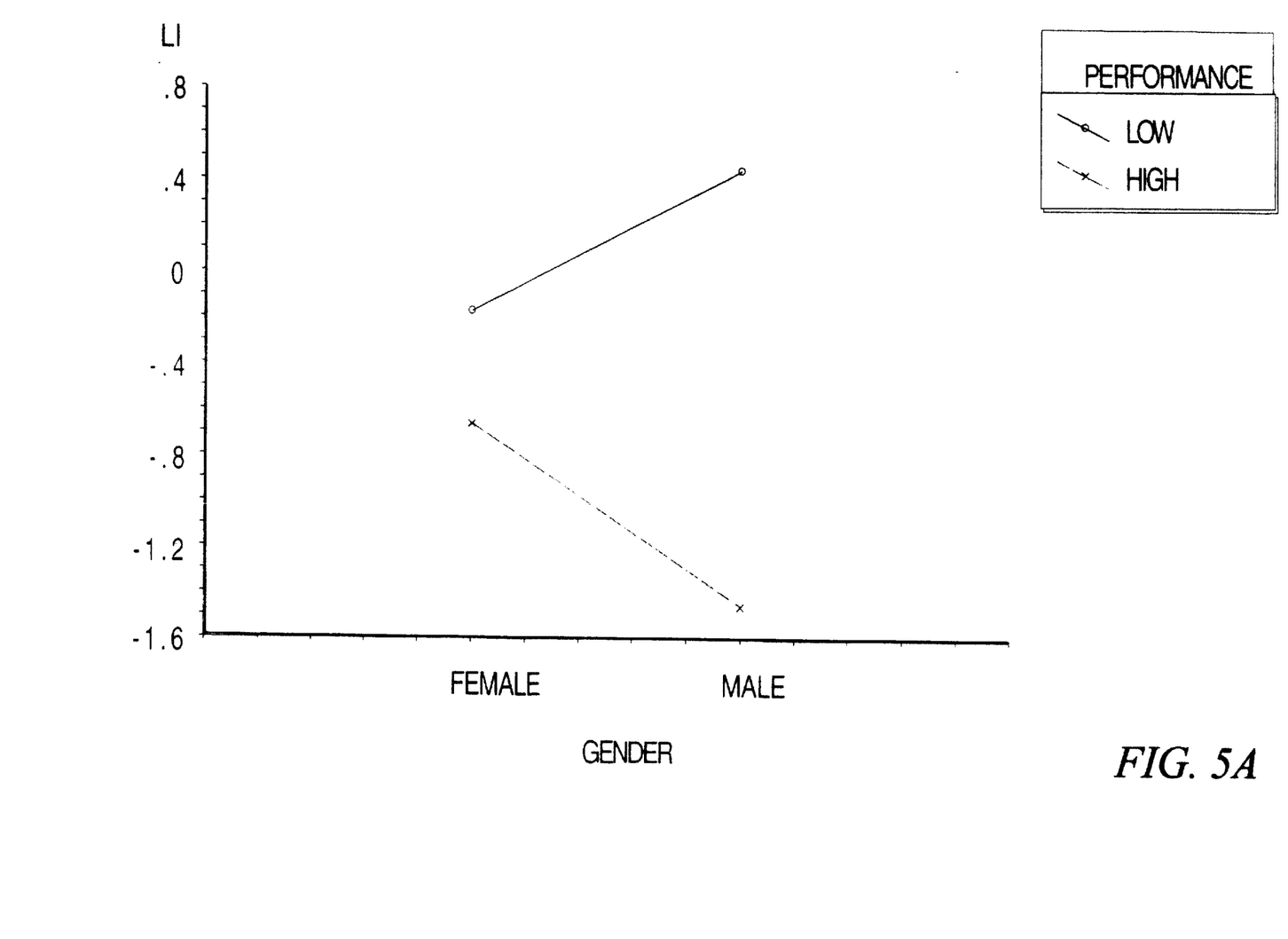
FIG. 5A shows the laterality index changes in females and males with low and high performance scores.
Figure 5B:
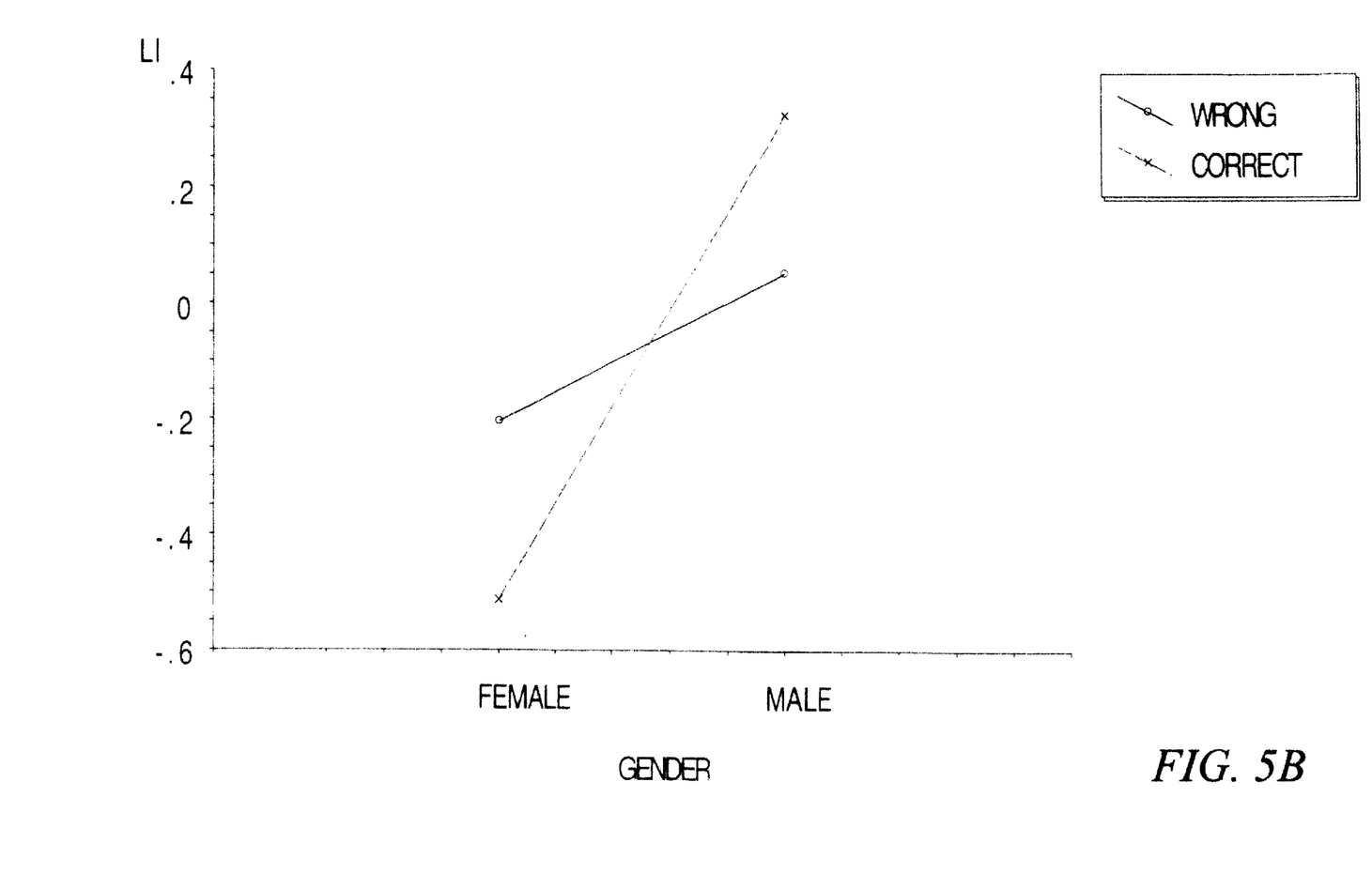
FIG. 5B shows the laterality index changes in females and males for wrong and correct answers to Raven's Progressive Matrices Test.

Low performance scores showed bi-hemispheric activation or a right tendency (Mean LI=0.09±1.8); in contrast, high performance scores showed left lateralization (Mean LI=−0.79±1.7), the difference between both performance levels was significant [$F(1,1150)=53.2$, $p=0.00000001$, MSe=172.5]. The results were then analyzed using a 2×2 MANOVA design. There was no overall main effect of Gender (Female, Male), however, there was a main effect of Performance (Low, High) [$F(1,1148)=61.2$, $p=0.00000001$, MSe=192.9]. There was a Gender×Performance interaction [$F(1,1148)=21.1$, $p=0.0000048$, MSe=66.6]. FIG. 5A shows the LI scores for female and male subjects with low and high performance respectively. Female subjects with low performance showed a right tendency, conversely female subjects with high performance scores were left lateralized. Similarly, males subjects with low performance scores were right lateralized but showed left lateralization with high performance scores. There was also a main effect of Answer (Wrong, Correct) [$F(1,1148)=26.5$, $p=0.0000003$, MSe=87.6]. Gender×Answer interaction [$F(1,1148)=3.8$, $p=0.05$, MSe=12.6]. FIG. 5B shows that females used a left cognitive strategy while males used a right cognitive strategy in solving RPM tasks. However, there was a bi-hemispheric tendency in both gender if the subjects could not solve the tasks or provided a wrong answer. The results suggest that TCD would be useful in the study of general intelligence.

Testing Psychomotor Functions

Materials and Methods

Bilateral simultaneous transcranial Doppler (TCD) ultrasound was used to measure mean blood flow velocities (MBFV) in the right (RMCA) and left (LMCA) middle cerebral arteries (MCA) in 14 (male=8, female=7; age 24±1.6 years) normal subjects who were strongly right-handed based on all right response to questions in the Edinburgh Handedness Inventory (Oldfield, 1971) . There was no report of substance abuse and alcoholism in subjects and their immediate families. All were non-smokers and had no history of long-term medication use (including contraceptives in females), neurological, cardiovascular or respiratory diseases. No subject ingested caffeine or nicotine at least 24 hours prior to the study.

Scanning Procedure

All TCD studies were performed similar to the procedure described above.

Motor Task Paradigms

The tasks comprised a sequence of motor paradigms involving movement of fingers in the right hand (RT), left hand (LT), and both hands synchronously (BS). The fingers' movements involved repetitive opposing movement of the tip of the thumb to the tip of the other fingers sequentially at a rate of about two such movements per second. An observer monitored the rate of performance of the motor tasks. The duration of resting baseline and each motor task was 60 seconds respectively, and there were no inter-stimuli intervals. Repetitive practice effect in the preparatory phase assured an acceptable rate of fingers' movements before the start of experimental runs.

Calculations

Trials during which errors of recording occurred were marked and removed. During analysis of results, 10 seconds segments of the waveform envelope were averaged for resting values and for each RPM task paradigm. The resulting six MBFV values for rest and each task respectively, were used for further calculations. The hemispheric lateralization was assessed using laterality index (LI') expressed as:

$$LI'=(\text{Right MBFV}_{10sec}-\text{Left MBFV}_{10sec}/(\text{Right MBFV}_{10sec}+\text{Left MBFV}_{10sec}))*100.$$

The actual magnitude of lateralization (LI) for each 10 seconds segment for each paradigm was calculated as the difference between LI' values measured during the 10 seconds segment of the task and the corresponding 10 seconds segment of rest (onset of rest corresponds with onset of motor task per minute):

$$LI=LI'\text{task}_{10sec}-LI'\text{rest}_{10sec}$$

In general, positive LI values suggest right lateralization, while negative LI values suggest left lateralization. Zero LI values showed no lateralization from the resting condition or possible bilateral response. The calculated LI were designated as $LI_{0-10sec}$, $LI_{11-20sec}$, $LI_{21-30sec}$, $LI_{31-40sec}$, $LI_{41-50sec}$, $LI_{51-60sec}$, for values measured for the time segment 0–10 seconds, 11–20 seconds, 21–30 seconds, 31–40 seconds, 41–50 seconds, 51–60 seconds respectively.

Statistical Data Analysis

Results were given as mean±SD where applicable. The LI scores were analyzed using t Test correlated samples. All statistical calculations were done using a statistical software package (Statistica, StatSoft, OK, USA).

Results

Right finger movement resulted in left lateralization LI=−0.22±2.4; conversely, left finger movement resulted in right lateralization LI=0.83±2.5, the difference was significant (P=0.0000995). Bilateral finger movements were not accompanied only tendency toward right lateralization LI=0.21±2.2.

Conclusions

Transcranial Doppler sonography detected that high performance during RPM paradigm was associated with left lateralized response while low performance during RPM paradigm yielded a tendency towards right hemisphere advantage or a bi-hemispheric response. While most female subjects used a left hemisphere strategy, most male subjects used a right hemisphere strategy. Both strategies were equally effective at low g tasks, but at high g only those with a left hemisphere strategy succeeded. These results suggest that, high g was restricted to neural system mechanisms within one hemisphere and could then be recruited by many different forms of cognitive processes. It is expected that both high g and low g tasks share activation of common working memory anatomic structures located probably bilaterally, however, further activation of left hemisphere structures are required to ensure success at high g, conversely a right hemisphere activation at low g. Transcranial Doppler also detected the overall contralateral motor control of finger movements, and reduced lateralization with bilateral finger movements as expected.

Figure 6:
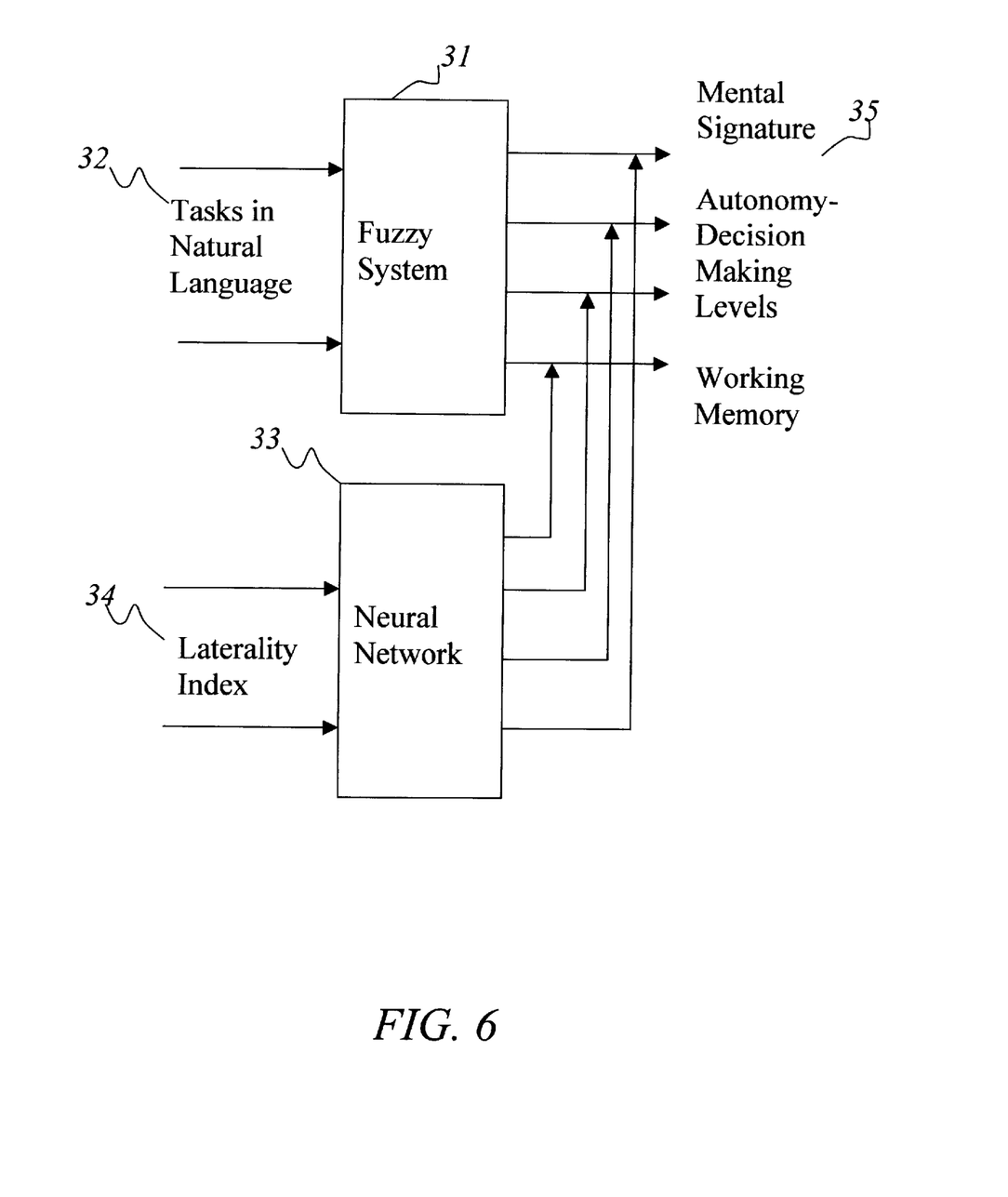
FIG. 6 is an example of a fuzzy system and neural network for processing perception and measurement based mental performance.

FIG. 6 shows an example of another application of the present invention using fuzzy systems 31 to process human perceptual tasks 32 presented in natural language and using neural network 33 to process inputs of cerebral blood flow velocity indices of mental performance 34 according to the teachings of the present invention. The outputs of the system 35 are used to determine the mental signature, autonomy-decision-making levels and working memory. The present invention uses the methodology described below to add to the measurement based mental performance, the capacity to operate on perception-based information. Human mental performance is dependent on perception of the presented task. Perception is intrinsically imprecise, reflecting the fundamental limitation on the cognitive ability of the human brain to resolve detail and store information. In more specific terms, perception and hence performance are, for the most part, f-granular, in the sense that (a) the values of attributes are granulated, with a granule being a clump of attribute-values which are drawn together by indistinguishability, similarity or proximity; and (b) the granules have unsharp (fuzzy) boundaries. For example, when a perceptual task is described, as "John is a young man," then Age is an f-granular variable, with granules of Age being very young, young, middle-aged, old, very old, etc.

F-granularity of perceptions cannot be expressed using conventional meaning-representation languages. For this reason, existing theories, including probability theory, and system theory, do not have a capability to operate on perception-based information. Basically, f-granulation may be viewed as a form of fuzzification, that is, progression from crisp sets in T to fuzzy sets in T, leading to an f.g-generalization of T which is denoted as $T^+$. For example, if T is probability theory, then in $T^+$ probabilities, functions, relations, intervals and everything else are allowed to have fuzzy denotations. Probabilities described as low, high, not very high, etc. could be interpreted as fuzzy sets of the unit interval, or equivalently, as possibility distributions of the numeric values. For example, f-granulation of an interval [1,3] of LI variability in probability theory T leads to an f-granulated interval in which the f-granules are labeled about 1, about 2, and about 3. Membership functions of such granules are usually assumed to be triangular or trapezoidal.

N1-granulation involves an addition to $T^{++}$ of the capacity to represent the meaning of a proposition, which describes a perception in a form that lends itself to computation. If perception the tasks are equated to their description in natural language, then operating on perceptions reduces to manipulations of propositions drawn from natural language in conjunction with the determined mental performance. This is realized through the use of fuzzy-logic-cased methodology referred to as computing with words (CW). The details of the approach of computing with words and the formulation of the computational theory of perception (CTP) has been described in an article by Zadeh L A, entitled 'From Computing with Numbers to Computing with Words. From Manipulation of Measurements to Manipulation of Perceptions' in a book edited by Marijuán P C. and entitled 'Cajal and Consciousness' and published in the Annals of the New York Academy of Sciences, New York, vol. 929, pages 221 through 252, 2001.

One way to apply the present invention is to use the neurocognitive strategy as the mental signature of the individual in conjunction with processing of the perception-based information of specially designed tasks. To allow access to a restricted network the individual could be presented with a series of tasks of which the mental signature of the subject is known. Confirmation of the mental signature will allow access to the network.

I claim:

1. A noninvasive method to determine the mental performance capacity of a human subject to perform a given task, including steps of:
    (a) obtaining a subject's baseline cerebral blood flow velocity in cerebral arteries on both sides of the brain using a transcranial Doppler ultrasound instrument with two probes placed on the temples and sample volumes focused on cerebral vessels on both sides;
    (b) simultaneously with (a) obtaining the mean blood flow velocity and calculating laterality index;
    (c) testing the subject with tasks of mental performance presented on the screen of a digital computer and using a computer input peripheral device while simultaneously monitoring the mean blood flow velocity during each stage of the task in real-time;
    (d) determining mental performance status using the laterality index calculated from mean cerebral blood flow velocity;
    (e) simultaneously with (d) assessing the task proficiency of the subject;
    (f) simultaneously with (e) determining the neurocognitive strategy of the subject during performance of the task;
    (g) simultaneously with (f) determining the change in neurocognitive strategy from prior measurements;
    (h) simultaneously with (g) determining if there is a corresponding rise in error rates during task performance; and
    (i) simultaneously with (h) assessing if the critical limit of neurocognitive workload has been reached.

2. The invention of claim 1 wherein the subject has a daily assignment and the subject is tested according to steps (a) and (b) each day prior to the subject's work assignment.

3. The invention of claim 1 wherein the subject is tested each time the subject logs on to the computer system according to steps (c), (d) and (e).

4. The invention of claim 1 wherein the tests of step (c) use a display which is displayed on the screen of a digital computer system and are selected from a group of working memory tests, intelligence tests, visuomotor tests, psychomotor tests, attentional tests and simulation tests.

5. The invention of claim 1 wherein the subject is tested according to steps (c), (d) and (e) and the task proficiency of the subject assessed by true or false responses displayed on the screen of a digital computer system.

6. The invention of claim 1 wherein the neurocognitive strategy of the subject determined according to step (f) is communicated to a remote computer or Internet using a cellular phone.

7. The invention of claim 1 wherein the transcranial Doppler ultrasound instrument according to step (a) is electrically powered by means of a rechargeable battery source or mains.

8. A noninvasive method to determine the mental performance capacity of a human subject to perform a given task, including steps of:
    (a) obtaining a subject's baseline cerebral blood flow velocity in cerebral arteries on both sides of the brain using a transcranial Doppler ultrasound instrument with two probes placed on the temples and sample volumes focused on cerebral vessels on both sides;
    (b) simultaneously with (a) obtaining the mean blood flow velocity in both cerebral arteries;
    (c) testing the subject with tasks of mental performance presented on the screen of a digital computer and using a computer input peripheral device while simultaneously monitoring the mean blood flow velocity during each stage of the task in real-time;
    (d) determining mental performance status by comparing the mean cerebral blood flow velocity obtained during the task to baseline mean blood flow velocity;
    (e) simultaneously with (d) assessing the task proficiency of the subject;
    (f) simultaneously with (e) determining the neurocognitive strategy of the subject during performance of the task;
    (g) simultaneously with (f) determining the change in neurocognitive strategy from prior measurements;
    (h) simultaneously with (g) determining if there is a corresponding rise in error rates during task performance;
    (i) simultaneously with (h) assessing if the critical limit of neurocognitive workload has been reached; and
    (j) simultaneously with (i) processing the neurocognitive workload data with a program stored in the system microprocessor.

9. The invention of claim 8 wherein the assessment of the critical limit of neurocognitive workload according to step (i) is used to determine the level of working memory attained under various treatment or training programs designed to improve the subject's productivity.

10. The invention of claim 8 wherein the subject is tested according to step (c) with tasks of mental performance selected from a group of linguistic and non-linguistic tests.

11. The invention of claim 8 wherein the determined error rates according to step (h) are used as an indices for objectively measuring skill acquisition and automation of a subject in order to optimize training programs.

12. The invention of claim 8 wherein the determined neurocognitive strategy according to step (f) is used as the mental signature or physiologic identity of the subject when the subject logs on a computer network.

13. The invention of claim 8 wherein a group of subjects are tested according to steps (c), (d) and (e) at various locations simultaneously and each subject's location determined using global positioning system.

14. A method to determine the mental performance capacity of a human subject to perform a given task, including steps of:
    (a) obtaining a subject's baseline cerebral blood flow velocity in cerebral arteries using a transcranial Doppler ultrasound instrument with sample volumes focused on cerebral vessels on both sides using two probes placed on the temples;
    (b) simultaneously with (a) obtaining the mean blood flow velocity and calculating laterality index;
    (c) testing the subject with tasks of mental performance presented on the screen of a digital computer and using computer input peripheral device selected from the group of a pressure key, a mouse, a keyboard, joystick or objects of virtual environment while simultaneously monitoring the mean blood flow velocity during each stage of the task in real-time;
    (d) determining mental performance status using the laterality index calculated from mean cerebral blood flow velocity;
    (e) simultaneously with (d) assessing the task proficiency of the subject;
    (f) simultaneously with (e) determining the neurocognitive strategy of the subject during performance of the task;

(g) simultaneously with (f) determining the change in neurocognitive strategy from prior measurements;

(h) simultaneously with (g) determining if there is a corresponding rise in error rates during task performance;

(i) simultaneously with (h) assessing if the critical limit of neurocognitive workload has been reached;

(j) simultaneously with (i) processing the neurocognitive workload data with a program stored in the system microprocessor; and (k) communicating the derived neurocognitive workload to another computer.

15. The invention of claim 14 wherein the derived neurocognitive workload is communicated to another computer according to step (k) in order to alter the mode of function of the program in the said computer.

16. The invention of claim 14 wherein the neurocognitive workload data are processed using a computer program according to step (j) selected from fuzzy and neural network systems for optimization of the production process.

17. The invention of claim 14 wherein the subject is tested according to steps (c), (d) and (e) in extreme environment as compared to tests according to steps (a) and (b) under normal conditions in order to examine the effects of extreme environment on mental performance.

18. The invention of claim 14 wherein the neurocognitive workload is communicated to a computer according to step (k) to alter the type and level of difficulty of a video game presented to the subject on the display of the said digital computer when the said neurocognitive workload exceeds the set critical limit according to step (i).

19. The invention of claim 14 wherein the neurocognitive workload is communicated to a computer according to step (k) in order to alter the autonomy-decision making level from the subject to an automated program or mission control when the said neurocognitive workload exceeds the set critical limit according to step (i).

20. The invention of claim 14 wherein the tests of step (c) use a display which is displayed on the screen of a digital computer system and are selected from a group of tests designed in virtual environment to evaluate cognitive, perceptual and motor abilities.

* * * * *